United States Patent
Guglielmotti et al.

(10) Patent No.: US 9,255,073 B2
(45) Date of Patent: *Feb. 9, 2016

(54) 1-BENZYL-3-HYDROXYMETHYLINDAZOLE DERIVATIVES AND USE THEREOF IN THE TREATMENT OF DISEASES BASED ON THE EXPRESSION OF MCP-1, CX3CR1 AND P40

(71) Applicant: AZIENDE CHIM. RIUN. ANG. FRANC. A.C.R.A.F. S.p.A., Rome (IT)

(72) Inventors: Angelo Guglielmotti, Rome (IT); Guido Furlotti, Rome (IT); Giorgina Mangano, Rome (IT); Nicola Cazzolla, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 139 days.

This patent is subject to a terminal disclaimer.

(21) Appl. No.: 13/898,950

(22) Filed: May 21, 2013

(65) Prior Publication Data

US 2013/0267704 A1   Oct. 10, 2013

Related U.S. Application Data

(63) Continuation of application No. 12/865,792, filed as application No. PCT/EP2009/052588 on Mar. 5, 2009, now Pat. No. 8,461,194.

(30) Foreign Application Priority Data

Mar. 7, 2008 (EP) .................................. 08425140

(51) Int. Cl.
| A61K 31/415 | (2006.01) |
| A01N 43/56 | (2006.01) |
| C07D 231/56 | (2006.01) |
| C07D 209/00 | (2006.01) |
| C07D 231/54 | (2006.01) |
| C07D 401/12 | (2006.01) |
| C07D 295/088 | (2006.01) |

(52) U.S. Cl.
CPC ............ *C07D 231/56* (2013.01); *C07D 231/54* (2013.01); *C07D 295/088* (2013.01); *C07D 401/12* (2013.01)

(58) Field of Classification Search
None
See application file for complete search history.

(56) References Cited

U.S. PATENT DOCUMENTS

| 6,534,534 B1 | 3/2003 | Guglielmotti et al. |
| 7,919,518 B2 | 4/2011 | Guglielmotti et al. |
| 8,283,348 B2 * | 10/2012 | Guglielmotti et al. ..... 514/234.5 |
| 8,314,099 B2 * | 11/2012 | Guglielmotti et al. ..... 514/234.5 |
| 8,354,544 B2 * | 1/2013 | Caracciolo Torchiarolo et al. ............... 548/362.5 |
| 8,461,194 B2 * | 6/2013 | Guglielmotti et al. ........ 514/405 |
| 8,569,297 B2 * | 10/2013 | Guglielmotti et al. ..... 514/234.5 |
| 2006/0047126 A1 | 3/2006 | Georg et al. |
| 2007/0015771 A1 | 1/2007 | Matteucci et al. |
| 2007/0043057 A1 | 2/2007 | Matteucci et al. |
| 2011/0003874 A1 | 1/2011 | Guglielmotti et al. |
| 2012/0171170 A1 | 7/2012 | Collard et al. |
| 2012/0220636 A1 | 8/2012 | Guglielmotti et al. |
| 2013/0012510 A1 | 1/2013 | Guglielmotti et al. |

FOREIGN PATENT DOCUMENTS

| EP | 0 382 276 B1 | 8/1995 |
| EP | 0 510 748 B1 | 3/1996 |
| EP | 1 185 528 | 3/2002 |
| EP | 1 188 438 A1 | 3/2002 |
| EP | 1 199 074 A1 | 4/2002 |
| EP | 1 005 332 B1 | 10/2003 |
| EP | 1 369 119 A1 | 12/2003 |
| EP | 1 458 687 | 9/2004 |
| EP | 1 675 862 | 7/2006 |
| EP | 1 819 341 | 8/2007 |
| EP | 1 827 447 | 9/2007 |
| EP | 1 869 055 | 12/2007 |
| EP | 1 869 056 | 12/2007 |
| WO | 99 04770 | 2/1999 |
| WO | WO 00/78757 A1 | 12/2000 |
| WO | WO 03/047516 A2 | 6/2003 |
| WO | WO 2005/033115 A1 | 4/2005 |
| WO | WO 2006/053227 A2 | 5/2006 |
| WO | WO 2006/060194 A1 | 6/2006 |
| WO | WO 2006/107257 A1 | 10/2006 |

(Continued)

OTHER PUBLICATIONS

Feldmann et al., Anti-TNF therapy: Where have we got to in 2005?, Journal of Autoimmunity 25.*
Bradley, TNF-mediated disease, J. Pathol. 2008; 214: 149-160.*

(Continued)

*Primary Examiner* — Svetlana M Ivanova

(74) *Attorney, Agent, or Firm* — Oblon, McClelland, Maier & Neustadt, L.L.P.

(57) ABSTRACT

The present invention relates to novel 1-benzyl-3-hydroxymethylindazole derivatives according to formula (I) described in the claims, and to a pharmaceutical composition comprising them, together with a pharmaceutically acceptable vehicle. In addition, the present invention relates to the use of 1-benzyl-3-hydroxymethylindazole derivatives for the preparation of a pharmaceutical composition that is active in the treatment of diseases based on the expression of MCP-1, CX3CR1 and p40, and to their use in a method for treating or preventing diseases based on the expression of MCP-1, CX3CR1 and p40.

27 Claims, No Drawings

(56) References Cited

FOREIGN PATENT DOCUMENTS

| WO | WO 2006/107258 A1 | 10/2006 |
|----|-------------------|---------|
| WO | WO 2008/052898 A1 | 5/2008  |

OTHER PUBLICATIONS

Humira drug label, Jan. 2008, available at http://www.accessdata.fda.gov/drugsatfda_docs/label/2008/125057s0110lbl.pdf.*
Kitching et al., IL-12p40 and IL-18 in Crescent Glomerulonephritis: IL-12p40 is the Key Th1-Defining Cytokine Chain, Whereas IL-18 Promotes Local Inflammation and Leukocyte Recruitment, J. Am. Soc. Nephrol. 16: 2023-2033, 2005.*
Barrett J. Rollins, "Chemokines", Blood, vol. 90, No. 3, Aug. 1, 1997, 23 Pages.
Marco Baggiolini, "Chemokines and Leukocyte Traffic", Nature, vol. 392, Apr. 9, 1998, pp. 565-568.
Craig Gerard et al., "Chemokines and Disease", Nature Immunology, vol. 2, No. 2, Feb. 2001, pp. 108-115.
Surendran Mahalingam et al., "Chemokines and Viruses: Friends or Foes?", Trends in Microbiology, vol. 11, No. 8, Aug. 2003, pp. 383-391.
Nestor E. Rulli et al., "Ross River Virus: molecular and Cellular Aspects of Disease Pathogenesis", Pharmacology and Therapeutics, vol. 107, 2005, pp. 329-342.
Toshihiro Nanki et al., "Migration of CX3CR1-Positive T Cells Producing Type 1 Cytokines and Cytotoxic Molecules into the Synovium of Patients with Rheumatoid Arthritis", Arthritis and Rheumatism, vol. 46, No. 11, Nov. 2002, pp. 2878-2883.
Stephan Segerer et al., "Expression of the Fractalkine Receptor (CX3CR1) in Human Kidney Diseases", Kidney International, vol. 62, 2002, pp. 488-495.
Miquel Sans et al., "Enhanced Recruitment of CX3CR1+ T Cells by Mucosal Endothelial Cell-Derived Fractalikine in Inflammatory Bowel Disease", Gastroenterology, vol. 132, No. 1, 2007, pp. 139-153.
Ping Liu et al., "Cross Talk Among Smad, MAPK, and Integrin Signaling Pathways Enhances Adventitial Fibroblast Functions Activated by Transforming Growth Factor $^2$1 and Inhibited by Gax", Arteriosclerosis, Thrombosis, and Vascular Biology, vol. 28, Jan. 10, 2008, 23 Pages.
David H. McDermott et al., "Chemokine Receptor Mutant CX3CR1-M280 has Impaired Adhesive Function and Correlates with Protection from Cardiovascular Disease in Humans", The Journal of Clinical Investigation, vol. 111, No. 8, Apr. 2003, pp. 1241-1250.
Alexander Niessner et al., "Wound Healing and Inflammation/Infection: Fractalkine Receptor Polymorphisms V249I and T280M as Genetic Risk Factors for Restenosis", Thrombosis and Haemostasis, vol. 94, 2005, pp. 1251-1256.
Dr. John Koo, "Population-Based Epidemiologic Study of Psoriasis with Emphasis on Quality of Life Assessment", Psychodermatology, vol. 14, No. 3, Jul. 1996, pp. 485-496.
Dr. Michael P. Schoen et al., "Medical Progress: Psoriasis", The New England Journal of Medicine, vol. 352, No. 18, May 5, 2005, pp. 1899-1912.
Marina Sironi et al., "A Small Synthetic Molecule Capable of Preferentially Inhibiting the Production of the CC Chemokine Monocyte Chemotactic Protein-1", European Cytokine Network, vol. 10, No. 3, Sep. 1999, pp. 437-441.
STN document No. 148:54890 to Fang et al., Nov. 26, 2007.
STN document No. 2006:194021, Mar. 3, 2006.
Golub et al, Science, vol. 286, Oct. 15, 1999, pp. 531-537.
Lala et al, Cancer and Metastasis Reviews (1998), 17(1) 91-106.
Henke, B. R. et al., "Optimization of 3-(1H-Indazol-3-ylmethyl)-1,5-Benzodiazepines As Potent, Orally Active CCK-A Agonists", Journal of Medicinal Chemistry, vol. 40, No. 17, pp. 2706-2725 (Aug. 15, 1997) XP 002105882.
Corsi, G. et al., "1-Halobenzyl-1H-Indazoles-3-Carboxylic Acids. A New Class of Antispermatogenic Agents", Journal of Medicinal Chemistry, vol. 19, No. 6, pp. 778-783 (1976) XP 002493577.
Janet Dawson, et al., "Targeting monocyte chemoattractant protein-1 signalling in disease", Expert Opin. Ther Targets (2003) 7(1), pp. 35-48.
Bok Yun Kang, et al., "Targeting Cytokines of the Interleukin-12 Family in Autoimmunity", Current Medicinal Chemistry, 2006, 13, 1149-1156.
Surendran Mahalingam, et al., Chemokines and Viruses: friends or foes?, Trends in Microbiology, vol. 11, No. 8, Aug. 2003, pp. 383-391.
Nestor E. Rulli, et al., "The Molecular and Cellular Aspecs of Arthritis Due to Alphavirus Infections", Ann. N.Y. Acad. Sci, 1102:96-108 (2007).
Elena Galkina, et al., "Leukocyte Recruitment and Vascular Injury in Diabetic Nephropathy", J. Am Soc Nephrol 17: 368-377 (2006).
Min Jeong Kim, et al., "Urinary monocyte chemoattractant protein-1 in renal disease", Clinca Chimica Acta 412(2011) 2022-2030.
A Richard Kitching, et al., "IL-12p40 and IL-18 in Crescentic Glomerulonephritis: IL-12p40 is the Key Th1-Defining Cytokine Chain, Whereas IL-18 Promotes Local Inflammation and Leukocyte Recruitment", J. Am Soc Nephrol16; 2023-2033,2005.
Rui-Xue Leng, et al., "IL-23: A Promising Therapeutic Target for Systemic Lupus Erythematosus", Archives of Medical Research, 41 (2010) 221-225.
Brad H. Rovin, et al., "Biomarker Discovery in Human SLE Nephritis", Bulletin of the NYU Hospital for Joint Diseases 2007;65(3):187-93.
Olga Stasikowska, et al., "Chemokines and chemokine receptors in glomerulonephritis and renal allograft rejection", Med Sci Monit, 2007; 13(2): RA31-36.
G.H. Tesch, "MCP-1/CCI2: a new diagnostic marker and therapeutic target for progressive renal injury in diabetic nephropathy", Am J Physiol Renal Physiol 294:F697-F701, 2008, Published Feb. 13, 2008.
Danxia Zheng, et al., "Urinary Excretion of Monocyte Chemoattractant Protein-1 in Autosomal Dominant Polycystic Kidney Disease", J Am Soc Nephrol14: 2588-2595, 2003.
Don Mahad, et al., "Modulating CCR2 and CCL2 at the blood-brain barrier: relevance for multiple sclerosis pathogenesis", Brain (2006), 129, 212-223.
Navneet Kaur Dhillon, et al., "Roles of MCP-1 in development of HIV-dementia", Front Bioscience 13:3913-3918, (Jul. 24, 2009).
Daniela Galimberti. et al., "Intrathecal Chemokine Synthesis in Mild Cognitive Impairment and Alzheimer Disease", Arch. Neurol. vol. 63 (Apr. 2006), pp. 538-543.
Murat Aral, et al., "The Relationship Between Serum Levels of Total IgE, IL-18, IL-12, IFN-γ and Disease Severity in Children With Atopic Dermatitis", Mediators of Inflammation, vol. 2006, Article ID 73098, pp. 1-4 (2006).
Dorothea C. Torti, et al., "Interleukin-12, interleukin-23, and psoriasis: Current prospects", J. Am Acad Dermatol (Dec. 2007), pp. 1059-1068.
Christian Vestergaard, et al., "Expression of CCR2 on Monocytes and Macrophages n Chronically Inflamed Skin in Atopic Dermatitis and Psoriasis", Acta Derm Venereol, 2004; 84: 353-358.
Jana Barlic, et al., "Chemokine regulation of atherosclerosis", Journal of Leukoeyte Biology vol. 82, Aug. 2007, pp. 226 236.
Israel F. Charo, et al., "Chemokines in the Pathogenesis of Vascular Disease", Circ. Res. 2004;95;858-866.
Kensuke Egashira, et al., "Molecular Mechanisms Mediating Inflammation in Vascular Disease: Special Reference to Monocyte Chemoattractant Protein-1", Hypertension 2003;41 ;834-841.
Hisanori Umehara, et al., "Fractalkine in Vascular Biology: From Basic Research to Clinical Disease", ArteriosclerThromb Vasc Biol., 2004, 24:34-40.
Peter J. Mannon, et al., "Anti-Interleukin-12 Antibody for Active Crohn's Disease", New England Journal of Medicine, 2004; 351-2069-79.
Mariagrazia Uguccioni, et al., "Increased Expression of IP-10, IL-8, MCP-1, and MCP-3 in Ulcerative Colitis", American Journal of Pathology, vol. 155, No. 2, Aug. 1999, pp. 331-336.

* cited by examiner

1-BENZYL-3-HYDROXYMETHYLINDAZOLE DERIVATIVES AND USE THEREOF IN THE TREATMENT OF DISEASES BASED ON THE EXPRESSION OF MCP-1, CX3CR1 AND P40

This application is a continuation application of U.S. application Ser. No. 12/865,792, filed Aug. 2, 2010, which is a national stage application of PCT/EP09/052588, filed Mar. 5, 2009, which claims priority to application EP 08425140.4, filed Mar. 7, 2008, the entire contents of which are incorporated herein by reference.

FIELD OF THE INVENTION

The present invention relates to 1-benzyl-3-hydroxymethylindazole derivatives, to a pharmaceutical composition comprising them, and to their use in the treatment of diseases based on the expression of MCP-1, CX3CR1 and p40.

In particular, the present invention relates to novel 1-benzyl-3-hydroxymethylindazole derivatives according to formula (I) below, and to a pharmaceutical composition comprising them together with a pharmaceutically acceptable vehicle. In addition, the present invention relates to the use of 1-benzyl-3-hydroxymethylindazole derivatives for preparing a pharmaceutical composition that is active in the treatment of diseases based on the expression of MCP-1, CX3CR1 and p40, and to their use in a method for treating or preventing diseases based on the expression of MCP-1, CX3CR1 and p40.

BACKGROUND OF THE ART

As is known, MCP-1 (Monocyte Chemotactic Protein-1) is a protein belonging to the β subfamily of chemokines. MCP-1 has powerful chemotactic action on monocytes and exerts its action also on T lymphocytes, mastocytes and basophils (Rollins B. J., Chemokines, Blood 1997; 90: 909-928; M. Baggiolini, Chemokines and leukocyte traffic, Nature 1998; 392: 565-568).

Other chemokines belonging to the β subfamily are, for example, MCP-2 (Monocyte Chemotactic Protein-2), MCP-3, MCP-4, MIP-1α and MIP-1β, RANTES.

The β subfamily differs from the α subfamily in that, in the structure, the first two cysteines are adjacent for the β subfamily, whereas they are separated by an intervening amino acid for the α subfamily.

MCP-1 is produced by various types of cells (leukocytes, platelets, fibroblasts, endothelial cells and smooth muscle cells).

Among all the known chemokines, MCP-1 shows the highest specificity for monocytes and macrophages, for which it constitutes not only a chemotactic factor but also an activation stimulus, consequently inducing processes for producing numerous inflammatory factors (superoxides, arachidonic acid and derivatives, cytokines/chemokines) and amplifying the phagocytic activity.

The secretion of chemokines in general, and of MCP-1 in particular, is typically induced by various pro-inflammatory factors, for instance interleukin-1 (IL-1), interleukin-2 (IL-2), TNFα (Tumour Necrosis Factor α), interferon-γ and bacterial lipopolysaccharide (LPS).

Prevention of the inflammatory response by blocking the chemokine/chemokine receptor system represents one of the main targets of pharmacological intervention (Gerard C. and Rollins B. J., Chemokines and disease. Nature Immunol. 2001; 2:108-115).

There is much evidence to suggest that MCP-1 plays a key role during inflammatory processes and has been indicated as a new and validated target in various pathologies.

Evidence of a considerable physiopathological contribution of MCP-1 has been obtained in the case of patients with articular and renal inflammatory diseases (rheumatoid arthritis, lupus nephritis, diabetic nephropathy and rejection following transplant).

However, more recently, MCP-1 has been indicated among the factors involved in inflammatory pathologies of the CNS (multiple sclerosis, Alzheimer's disease, HIV-associated dementia) and other pathologies and conditions, with and without an obvious inflammatory component, including atopic dermatitis, colitis, interstitial lung pathologies, restenosis, atherosclerosis, complications following a surgical intervention (for instance angioplasty, arterectomy, transplant, organ and/or tissue replacement, prosthesis implant), cancer (adenomas, carcinomas and metastases) and even metabolic diseases such as insulin resistance and obesity.

In addition, despite the fact that the chemokine system is involved in controlling and overcoming viral infections, recent studies have demonstrated that the response of certain chemokines, and in particular of MCP-1, may have a harmful role in the case of host-pathogen interactions. In particular, MCP-1 has been indicated among the chemokines that contribute towards organ and tissue damage in pathologies mediated by alpha viruses characterized by monocyte/macrophage infiltration in the joints and muscles (Mahalingam S. et al. Chemokines and viruses: friend or foes? Trends in Microbiology 2003; 11: 383-391; Rulli N. et al. Ross River Virus: molecular and cellular aspects of disease pathogenesis. 2005; 107: 329-342).

Monocytes are the main precursors of macrophages and dendritic cells, and play a critical role as mediators of inflammatory processes. CX3CR1, with its ligand CX3CL1 (fractalkine), represents a key factor in regulating the migration and adhesiveness of monocytes. CX3CR1 is expressed in monocytes, whereas CX3CL1 is a transmembrane chemokine in endothelial cells. Genetic studies in man and in animal models have demonstrated an important role in the physiopathology of inflammatory diseases of CX3CR1 and CX3CL1. There is in fact much evidence to suggest a key contribution of CX3CR1 and of its ligand in the pathogenesis and progression of articular, renal, gastrointestinal and vascular inflammatory diseases (e.g. rheumatoid arthritis, lupus nephritis, diabetic nephropathy, Crohn's disease, ulcerative colitis, restenosis and atherosclerosis).

The expression of CX3CR1 is over-regulated in T cells, which are believed to accumulate in the synovium of patients suffering from rheumatoid arthritis. In addition, the expression of CX3CL1 is over-regulated in endothelial cells and fibroblasts present in the synovium of these patients. Consequently, the CX3CR1/CX3CL1 system plays an important role in controlling the type of cell and the mode of infiltration of the synovium and contributes towards the pathogenesis of rheumatoid arthritis (Nanki T. et al., "Migration of CX3CR1-positive T cells producing type 1 cytokines and cytotoxic molecules into the synovium of patients with rheumatoid arthritis", Arthritis & Rheumatism (2002), vol. 46, No. 11, pp. 2878-2883).

In patients suffering form renal damage, the majority of the inflammatory leukocytes that infiltrate the kidneys express CX3CR1, and in particular it is expressed on two of the main cell types involved in the most common inflammatory renal pathologies and in kidney transplant rejection, T cells and monocytes (Segerer S. et al., Expression of the fractalkine receptor (CX3CR1) in human kidney diseases, Kidney International (2002) 62, pp. 488-495).

Participation of the CX3CR1/CX3CL1 system has been suggested also in inflammatory bowel diseases (IBD). In point of fact, in the case of patients suffering from IBD (e.g. Crohn's disease, ulcerative colitis), a significant increase in the production of CX3CL1 by the intestinal capillary system and a significant increase in CX3CR1-positive cells have been demonstrated, both at the circulatory level and in the mucosa (Sans M. et al., "Enhanced recruitment of CX3CR1+T cells by mucosal endothelial cell-derived fractalkine in inflammatory bowel diseases", Gastroenterology 2007, vol. 132, No. 1, pp. 139-153).

Even more interesting is the demonstration of the key role played by the CX3CR1/CX3CL1 system in vascular damage and in particular under pathological conditions, for instance atherosclerosis and restenosis. CX3CR1 is indicated as a critical factor in the process of infiltration and accumulation of monocytes in the vascular wall, and CX3CR1 polymorphism in man is associated with a reduced prevalence of atherosclerosis, coronary disorders and restenosis (Liu P. et al., "Cross-talk among Smad, MAPK and integrin signalling pathways enhances adventitial fibroblast functions activated by transforming growth factor-1 and inhibited by Gax" Arterioscler. Thromb. Vasc. Biol. 2008; McDermott D. H. et al., "Chemokine receptor mutant CX3CR1-M280 has impaired adhesive function and correlates with protection from cardiovascular diseases in humans", J. Clin. Invest. 2003; Niessner A. et al., Thrombosis and Haemostasis 2005).

IL-12 and IL-23 are members of a small family of proinflammatory heterodimeric cytokines. Both cytokines share a common subunit, p40, which is covalently bonded either to the p35 subunit to produce the mature form of IL-12, or to the p19 subunit to produce the mature form of IL-23. The receptor for IL-12 is constituted by the subunits IL-12Rβ1 and IL-12Rβ2, while the receptor for IL-23 is constituted by the subunits IL-12Rβ1 and IL-23R.

IL-12 and IL-23 are mainly expressed by activated dendritic cells and by phagocytes. The receptors for the two cytokines are expressed on the T and NK cells, and NK T cells, but low levels of complexes of the receptor for IL-23 are also present in monocytes, macrophages and dendritic cells.

Despite these similarities, there is much evidence to suggest that IL-12 and IL-23 control different immunological circuits. In point of fact, whereas IL-12 controls the development of Th1 cells, which are capable of producing gamma-interferon (IFN-γ), and increases the cytotoxic, antimicrobial and antitumoral response, IL-23 regulates a circuit that leads to the generation of CD4$^+$ cells, which are capable of producing IL-17. The induction of IL-23-dependent processes leads to the mobilization of various types of inflammatory cell, for instance $T_H$-17, and it has been demonstrated as being crucial for the pathogenesis of numerous inflammatory pathologies mediated by immonological responses.

Typical examples of pathologies associated with the expression of p40 are chronic inflammatory diseases of the articular apparatus (e.g. rheumatoid arthritis), of the dermatological apparatus (e.g. psoriasis) and of the gastrointestinal apparatus (e.g. Crohn's disease). However, IL-23 also exerts a role in promoting tumour incidence and growth. In point of fact, IL-23 regulates a series of circuits in the tumoral microenvironment, stimulating angiogenesis and the production of inflammation mediators.

Psoriasis is a chronic inflammatory skin disease that affects 3% of the world's population (Koo J. Dermatol. Clin. 1996; 14:485-96; Schon M. P. et al., N. Engl. J. Med. 2005; 352: 1899-912). A type-1 aberrant immune response has been correlated with the pathogenesis of psoriasis, and the cytokines that induce this response, such as IL-12 and IL-23, may represent suitable therapeutic objects. The expression of IL-12 and IL-23, which share the subunit p40, is significantly increased in psoriasis plaques, and preclinical studies have demonstrated a role of these cytokines in the pathogenesis of psoriasis. More recently, the treatment of anti-IL-12 and IL-23 monoclonal antibodies of patients suffering from psoriasis proved to be effective in improving the signs of progression and seriousness of the disease and has subsequently reinforced the role of IL-12 and IL-23 in the physiopathology of psoriasis.

Crohn's disease is a chronic inflammatory pathology of the digestive apparatus and may affect any region thereof—from the mouth to the anus. It typically afflicts the terminal tract of the ileum and well-defined areas of the large intestine. It is often associated with systemic autoimmune disorders, such as mouth ulcers and rheumatic arthritis. Crohn's disease affects over 500 000 people in Europe and 600 000 people in the United States.

Crohn's disease is a pathology associated with a Th1 cell-mediated excessive activity of cytokines. IL-12 is a key cytokine in the initiation of the inflammatory response mediated by Th1 cells. Crohn's disease is characterized by increased production of IL-12 by cells presenting the antigen in intestinal tissue, and of gamma-interferon (IFN-γ) and TNFα by lymphocytes and intestinal macrophages. These cytokines induce and support the inflammatory process and thickening of the intestinal wall, which are characteristic signs of the pathology. Preclinical and clinical evidence has demonstrated that inhibition of IL-12 is effective in controlling the inflammatory response in models of intestinal inflammation and/or in patients suffering from Crohn's disease.

The relationship between cancer and inflammation is now an established fact. Many forms of tumours originate from sites of inflammation, and inflammation mediators are often produced in tumours.

IL-23 has been identified as a cytokine associated with cancer and, in particular, the expression of IL-23 is significantly high in samples of human carcinomas when compared with normal adjacent tissues. In addition, the absence of a significant expression of IL-23 in the normal adjacent tissues suggests an over-regulation of IL-23 in tumours, reinforcing its role in tumour genesis.

European patent EP-B-0 382 276 describes a number of 1-benzyl-3-hydroxymethylindazole derivatives endowed with analgesic activity. In turn, European patent EP-B-0 510 748 describes, on the other hand, the use of these derivatives for preparing a pharmaceutical composition that is active in the treatment of autoimmune diseases. Finally, European patent EP-B-1 005 332 describes the use of these derivatives for preparing a pharmaceutical composition that is active in treating diseases derived from the production of MCP-1. 2-Methyl-2-{[1-(phenylmethyl)-1H-indazol-3-yl]methoxy}propanoic acid is thought to be capable of inhibiting, in a dose-dependent manner, the production of MCP-1 and TNF-α induced in vitro in monocytes from LPS and *Candida albicans*, whereas the same compound showed no effects in the production of cytokines IL-1 and IL-6, and of chemokines IL-8, MIP-1α, and RANTES (Sironi M. et al., "A small synthetic molecule capable of preferentially inhibiting the production of the CC chemokine monocyte chemotactic protein-1", European Cytokine Network. Vol. 10, No. 3, 437-41, September 1999).

European patent application EP-A-1 185 528 relates to the use of triazine derivatives for inhibiting the production of IL-12. European patent application EP-A-1 188 438 and EP- A-1 199 074 relate to the use of inhibitors of the enzyme PDE4, for instance Rolipram, Ariflo and diazepine-indole derivatives, in the treatment and prevention of diseases associated with excessive production of IL-12. European patent application EP-A-1 369 119 relates to the use of hyaluronane with a molecular weight of between 600 000 and 3 000 000 daltons for controlling and inhibiting the expression of IL-12. European patent application EP-A-1 458 687 relates to the use of pyrimidine derivatives for treating diseases related to an overproduction of IL-12. European patent application EP-A-1 819 341 relates to the use of nitrogenous heterocyclic compounds, for instance pyridine, pyrimidine and triazine derivatives, for inhibiting the production of IL-12 (or of other cytokines, such as IL-23 and IL-27 which stimulate the production of IL-12). European patent application EP-A-1 827 447 relates to the use of pyrimidine derivatives for treating diseases related to an overproduction of IL-12, IL-23 and IL-27.

European patent applications EP-A-1 869 055, EP-A-1 869 056 and EP-A-1 675 862 describe 1,3-thiazolo-4,5-pyrimidine derivatives that are capable of acting as CX3CR1 receptor antagonists.

The preparation of compound [1-(2,4-dichlorobenzyl)-1H-indazol-3-yl]methanol is described in patent applications US2007/0015771 and US2007/0043057 (compound 58). Compound 58 is used as an intermediate for syntheses of aldehyde derivatives, and is not associated with any pharmacological activity.

The preparation of compound (1-benzyl-1H-indazol-3-yl)methanol is described in Henke B. R. et al.; "Optimization of 3-(1H-Indazol-3-ylmethyl)-1,5-benzodiazepines as Potent, Orally Active CCK-A Agonists." Journal of Medicinal Chemistry (1997), 40(17), 2706-2725 (compound 59). Compound 59 is used as an intermediate for syntheses of benzodiazepine, and is not associated with any pharmacological activity.

The preparation of compound [1-(4-chlorobenzyl)-1H-indazol-3-yl]methanol is described in Corsi G, Palazzo G.; "1-halobenzyl-1H-indazoles-3-carboxylic acids. A new class of antispermatogenic agents". Journal of Medicinal Chemistry (1976), 19(6), 778-783 (compound 46). Compound 46 is used as an intermediate for the synthesis of carboxylic derivatives, and is not associated with any pharmacological activity.

Despite the activity developed thus far, there is still felt to be a need for novel pharmaceutical compositions and compounds that are effective in the treatment of diseases based on the expression of MCP-1, CX3CR1 and p40.

The Applicant has found, surprisingly, novel 1-benzyl-3-hydroxymethylindazole derivatives with pharmacological activity.

The Applicant has found, surprisingly, that the 1-benzyl-3-hydroxymethylindazole derivatives according to formula (I) of the present invention are capable of reducing the production of the chemokine MCP-1.

More surprisingly, the Applicant has found that the 1-benzyl-3-hydroxymethylindazole derivatives according to formula (I) of the present invention are capable of reducing the expression of the chemokine MCP-1.

Even more surprisingly, the Applicant has found that the 1-benzyl-3-hydroxymethylindazole derivatives according to formula (I) of the present invention are capable of reducing the expression of the subunit p40 involved in the production of the cytokines IL-12 and IL-23, and the expression of the receptor CX3CR1.

Thus, in a first aspect, the present invention consists of a compound of formula (I)

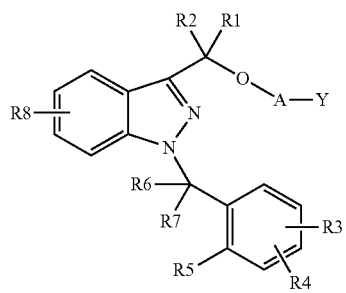

in which:
A may be a bond σ, —$X_1$— or —$X_1$—O—$X_2$—, in which
$X_1$ and $X_2$, which may be identical or different each other, may be an alkyl group having from 1 to 5 carbon atoms, optionally substituted with one or more alkyl groups having from 1 to 5 carbon atoms or one or more alkoxy groups having from 1 to 3 carbon atoms, Y is H when A is a bond σ, or Y may be H, —OH, or —N($R_{11}$)($R_{12}$), when A is —$X_1$— or —$X_1$—O—$X_2$—,
in which
$R_{11}$ may be hydrogen, an alkyl group having from 1 to 5 carbon atoms, or $R_{11}$ together with $R_{12}$ forms a 4- to 7-membered heterocycle,
$R_{12}$ may be hydrogen, an alkyl group having from 1 to 5 carbon atoms, or $R_{12}$ together with $R_{11}$ forms a 4- to 7-membered heterocycle,
$R_1$ and $R_2$, which may be identical or different each other, may be hydrogen, an alkyl group having from 1 to 5 carbon atoms,
$R_3$, $R_4$ and $R_8$, which may be identical or different each other, may be hydrogen, an alkyl group having from 1 to 5 carbon atoms, an alkoxy group having from 1 to 3 carbon atoms, a halogen atom, —OH, —N(R')(R''), —N(R')COR'', —CN, —CONR'R'', —$SO_2$NR'R'', —$SO_2$R', nitro and trifluoromethyl; with R' and R'', which may be identical or different each other, represented by hydrogen and an alkyl group having from 1 to 5 carbon atoms,
$R_5$ may be hydrogen, an alkyl group having from 1 to 5 carbon atoms, an alkoxy group having from 1 to 3 carbon atoms, a halogen atom, —OH, —N(R')(R''), —N(R')COR'', nitro and trifluoromethyl, or $R_5$ together with one from between $R_6$ and $R_7$ forms a ring having 5 or 6 carbon atoms; with R' and R'', which may be identical or different each other, represented by hydrogen and an alkyl group having from 1 to 5 carbon atoms,
$R_6$ and $R_7$, which may be identical or different each other, may be hydrogen, an alkyl group having from 1 to 5 carbon atoms, or together form a group C=O, or one from between $R_6$ and $R_7$, together with $R_5$, forms a ring having 5 or 6 carbon atoms,
with the proviso that when A is a bond σ, and Y, $R_1$, $R_2$, $R_6$, and $R_7$ are hydrogen atoms,
if $R_8$ is a hydrogen atom, then the group linked to the nitrogen atom in the 1-position of the indazole ring is different from a benzyl group, a 4-chlorobenzyl group, or a 2-4-dichlorobenzyl group,
if $R_8$ is a fluorine atom in the 5-position of the indazole ring, then the group linked to the nitrogen atom in the 1-position of the indazole ring is different from 5-chloro-2-methoxybenzyl group, and
if $R_8$ is a trifluoromethyl group in the 6-position of the indazole ring, then the group linked to the nitrogen atom in the 1-position of the indazole ring is different from a 2-4-dichlorobenzyl group.

In a second aspect, the present invention relates to a pharmaceutical composition comprising the novel 1-benzyl-3-hydroxymethylindazole derivatives according to formula (I) or a pharmaceutically acceptable salt thereof together with at least one pharmaceutically acceptable vehicle.

The over-regulation and/or the increase of the expression of the above mentioned MCP-1, CX3CR1, and p40, the latest resulting consequently in IL-12 and/or IL-23 expression/production, which results in a development of a pathology and/or a disease is often referred in the art with the term "overexpression". For the purpose of the present invention, the term expression is intended to include overexpression as known in the art.

Surprisingly, the Applicant has found that the 1-benzyl-3-hydroxymethylindazole derivatives according to formula (1) of the present invention may be used for the preparation of a pharmaceutical composition that is active in the treatment of diseases based on the expression of the chemokine MCP-1, of the subunit p40, and consequently of the cytokines IL-12 and IL-23, and of the receptor CX3CR1.

Thus, in a third aspect, the present invention relates to the use of a compound of formula (I)

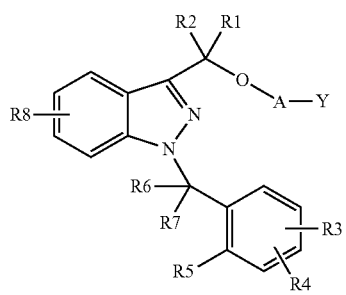

(I)

in which:

A may be a bond σ, —$X_1$— or —$X_1$—O—$X_2$—, in which $X_1$ and $X_2$, which may be identical or different each other, may be an alkyl group having from 1 to 5 carbon atoms, optionally substituted with one or more alkyl groups having from 1 to 5 carbon atoms or one or more alkoxy groups having from 1 to 3 carbon atoms, Y is H when A is a bond σ, or Y may be H, —OH, or —N($R_{11}$)($R_{12}$), when A is —$X_1$— or —$X_1$—O—$X_2$—, in which $R_{11}$ may be hydrogen, an alkyl group having from 1 to 5 carbon atoms, or $R_{11}$ together with $R_{12}$ forms a 4- to 7-membered heterocycle, $R_{12}$ may be hydrogen, an alkyl group having from 1 to 5 carbon atoms, or $R_{12}$ together with $R_{11}$ forms a 4- to 7-membered heterocycle, $R_1$ and $R_2$, which may be identical or different each other, may be hydrogen, an alkyl group having from 1 to 5 carbon atoms, $R_3$, $R_4$ and $R_5$, which may be identical or different each other, may be hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —$SO_2$NR'R", —$SO_2$R', nitro and trifluoromethyl; with R' and R", which may be identical or different each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, —OH, —N(R')(R"), —N(R')COR", nitro and trifluoromethyl, or $R_5$ together with one from between $R_6$ and $R_7$ forms a ring having 5 or 6 carbon atoms; with R' and R", which may be identical or different each other, represented by hydrogen and an alkyl group having from 1 to 5 carbon atoms, $R_6$ and $R_7$, which may be identical or different each other, may be hydrogen, an alkyl group having from 1 to 5 carbon atoms, or together form a group C═O, or one from between $R_6$ and $R_7$, together with $R_5$, forms a ring having 5 or 6 carbon atoms, for preparing a pharmaceutical composition for the treatment of diseases based on the expression of MCP-1, CX3CR1 and p40.

In addition, in a fourth aspect, the present invention relates to a method for treating or preventing diseases based on the expression of MCP-1, CX3CR1 and p40, characterized by the administration to a person in need thereof an effective amount of the compound of formula (I) previously described.

DETAILED DESCRIPTION OF THE INVENTION

In formula (I) previously described, residue A is represented by a bond σ, the group —$X_1$— or the group —$X_1$—O—$X_2$—.

Preferably, in formula (I) previously described, $X_1$ and $X_2$ are, independently of one another, an alkyl group having from 1 to 4 carbon atoms, optionally substituted with one or more alkyl groups having from 1 to 3 carbon atoms or one or more alkoxy groups having 1 or 2 carbon atoms.

More preferably, $X_1$ is a group $CH_2$, a group $CH_2CH_2$, a group $C(CH_3)_2$, or a group $C(CH_3)_2CH_2$, and $X_2$ is a group $CH_2$, a group $CH_2CH_2$ or a group $CH_2CH_2CH_2$.

Advantageously, in formula (I) previously described, residue A is represented by a bond σ, a group $CH_2CH_2$, a group $CH_2CH_2CH_2$, a group $C(CH_3)_2CH_2$, a group $CH_2CH_2OCH_2$, a group $CH_2CH_2OCH_2CH_2$, a group $C(CH_3)_2CH_2OCH_2$, and a group $C(CH_3)_2CH_2OCH_2CH_2$.

In formula (I) previously described, when A is a bond σ, then Y is a hydrogen atom, while when A is —$X_1$— or —$X_1$—O—$X_2$— then Y may be hydrogen, —OH, or —N($R_{11}$)($R_{12}$).

Advantageously, $R_{11}$ is represented by a hydrogen atom, an alkyl group having from 1 to 3 carbon atoms, or $R_{11}$ together with $R_{12}$ forms a 5- or 6-membered heterocycle.

Advantageously, $R_{12}$ is represented by a hydrogen atom, an alkyl group having from 1 to 3 carbon atoms, or $R_{12}$ together with $R_{11}$ forms a 5- or 6-membered heterocycle.

Preferably, $R_1$ and $R_2$, which may be identical or different, are represented by a hydrogen atom, an alkyl group having from 1 to 3 carbon atoms.

Preferably, $R_3$, $R_4$ and $R_8$, which may be identical or different, are represented by a hydrogen atom, an alkyl group having from 1 to 3 carbon atoms, an alkoxy group having 1 or 2 carbon atoms, a Br, Cl or F atom, the OH group, the nitro group, the trifluoromethyl group or the group N(R')(R"), —N(R')COR"; —CN, —CONR'R", —$SO_2$NR'R", —$SO_2$R', with R' and R", which may be identical or different, represented by a hydrogen atom and an alkyl group having from 1 to 3 carbon atoms.

Advantageously, $R_5$ is represented by a hydrogen atom, an alkyl group having from 1 to 3 carbon atoms, an alkoxy group having 1 or 2 carbon atoms, a halogen atom, an OH group, or $R_5$, together with one from between $R_6$ and $R_7$, forms a ring having 5 or 6 carbon atoms.

Preferably, $R_6$ and $R_7$, which may be identical or different, are represented by a hydrogen atom, an alkyl group having from 1 to 3 carbon atoms, or together form a group C=O, or one from between $R_6$ and $R_7$, together with $R_5$, forms a ring having 5 or 6 carbon atoms.

In the case of certain substituents, the compound of formula (I) according to the present invention may be an asymmetric carbon atom and may then be in the form of stereoisomers and enantiomers.

Depending on the nature of the substituents, the compound of formula (I) may form addition salts with physiologically acceptable organic or mineral acids or bases.

Typical examples of suitable physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable mineral bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

Depending on the nature of the substituents, the compound of formula (I) may form esters with physiologically acceptable organic acids. Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

The compounds of the present invention also include the prodrugs, stereoisomers, enantiomers and pharmaceutically acceptable salts or esters of the compounds represented by formula (I) described in the claims. The prodrug of a compound of formula (I) is a substance in substantially inactive form, which, when administered to a living being, is metabolized into a compound of formula (I).

The terms "pharmaceutically acceptable" and "physiologically acceptable" are intended to define, without any particular limitation, any material suitable for preparing a pharmaceutical composition to be administered to a living being.

The compounds according to formula (I) of the present invention may be used for the preparation of a pharmaceutical composition that is active in the treatment of diseases (or pathologies) based on the expression of the chemokine MCP-1, the cytokine p40, the subunit p40 (involved in the production of cytokines IL-12 and IL-23) and the receptor CX3CR1.

Preferably, the pathologies associated with the expression of MCP-1 and CX3CR1 are articular diseases, renal diseases, cardiovascular diseases, metabolic syndrome, obesity, diabetes, insulin resistance and cancer.

In particular, the pathologies associated with the expression of MCP-1 are rheumatoid arthritis, arthritis induced by viral infections, psoriatic arthritis, arthrosis, lupus nephritis, diabetic nephropathy, glomerulonephritis, polycystic kidney disease, interstitial lung disease, fibrosis, multiple sclerosis, Alzheimer's disease, HIV-associated dementia, atopic dermatitis, psoriasis, vasculitis, restenosis, atherosclerosis, myocardial infarction, angina, acute coronary diseases, adenomas, carcinomas and metastases, metabolic diseases and complications following surgical interventions such as, for example, angioplasty, arterectomy, circulation recovery techniques, transplants, organ replacements, tissue replacements and prosthesis implants.

In particular, the pathologies associated with the expression of CX3CR1 are rheumatoid arthritis, lupus nephritis, diabetic nephropathy, Crohn's disease, ulcerative colitis, coronary disorders, restenosis, atherosclerosis, myocardial infarction, angina, and complications following surgical interventions such as, for example, angioplasty, arterectomy and circulation recovery techniques.

Preferably, the pathologies associated with the expression of p40, and thus of IL-12 and IL-23, are autoimmune diseases, such as chronic degenerative inflammatory diseases, and cancer.

In particular, the pathologies associated with the expression of p40 are rheumatoid arthritis, psoriasis, glomerulonephritis, diabetes, lupus erythematosus, diabetes, Crohn's disease, and tumours such as, for example, colon carcinomas, breast carcinomas, lung carcinomas and prostate carcinomas, and skin and CNS neoplasias.

Preferably, the pharmaceutical compositions of the present invention are prepared in suitable dosage forms comprising an effective dose of at least one compound of formula (I), or a pharmaceutically acceptable salt, ester or prodrug thereof, and at least one pharmaceutically acceptable vehicle.

Examples of pharmaceutically acceptable vehicles known in the prior art are, for example, glidants, binders, disintegrants, fillers, diluents, flavourings, colorants, fluidizers, lubricants, preserving agents, humectants, absorbents and sweeteners.

Useful examples of pharmaceutically acceptable excipients are sugars, such as lactose, glucose or sucrose, starches, such as corn starch and potato starch, cellulose and derivatives thereof, for instance sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols such as propylene glycol, polyols such as glycerol, sorbitol, mannitol and polyethylene glycol, esters such as ethyl oleate and ethyl laurate, agar-agar, and the like.

Examples of suitable dosage forms are tablets, capsules, coated tablets, granules, solutions and syrups for oral administration; medicated plasters, solutions, pastes, creams and ointments for transdermal administration; suppositories for rectal administration and sterile solutions for injection or aerosol administration.

Other suitable dosage forms are sustained-release forms and liposome-based forms, for either the oral or injection route.

The dosage forms may also contain other conventional ingredients such as: preserving agents, stabilizers, surfactants, buffers, osmotic pressure regulators, emulsifiers, sweeteners, colorants, flavourings and the like.

When required for particular therapies, the pharmaceutical composition of the present invention may contain other pharmacologically active ingredients whose simultaneous administration is useful.

The amount of compound of formula (I) or of pharmaceutically acceptable salt, ester or prodrug thereof in the pharmaceutical composition of the present invention may vary within a wide range as a function of known factors, for instance the type of pathology to be treated, the severity of the disease, the body weight of the patient, the dosage form, the chosen route of administration, the number of daily administrations and the efficacy of the chosen compound of formula (I). However, the optimum amount may be determined simply and routinely by a person skilled in the art.

Typically, the amount of compound of formula (I) or of pharmaceutically acceptable salt, ester or prodrug thereof in the pharmaceutical composition of the present invention will be such that it ensures a level of administration of between 0.001 and 100 mg/kg/day. Preferably, the level of administration is between 0.05 and 50 mg/kg/day and even more preferably between 0.1 and 10 mg/kg/day.

The dosage forms of the pharmaceutical composition of the present invention may be prepared according to techniques that are well known to pharmaceutical chemists, including mixing, granulation, compression, dissolution, sterilization and the like.

The activity of the compounds of the present invention on MCP-1 and CX3CR1 was demonstrated in vitro in human monocytes via techniques of gene expression analysis with "real-time" RT-PCR and by protein production analysis via an immunoenzymatic test. As is known to those skilled in the art, the abovementioned experimental models are considered useful for checking the activity of the compounds with regard to the expression and production of MCP-1 and the expression of CX3CR1. Consequently, the abovementioned models may be considered as predictive of the activity in man for the treatment of pathologies characterized by the expression and production of MCP-1, by the expression of CX3CR1 and by inflammatory conditions with the presence of infiltrates rich in monocytes and macrophages.

The activity of the compounds of the present invention on p40 was demonstrated in vitro in human monocytes via gene expression analysis techniques with "real-time" RT-PCR. As is known to those skilled in the art, the abovementioned experimental model is useful for checking the activity of compounds with regard to the expression of p40 and may be considered as predictive of the activity in man for the treatment of pathologies characterized by the expression of p40.

The preparation of the compounds of general formula (I) may be performed according to one of the following procedures. Method (A) is applied when substituent A of formula (I) is equal to a bond σ. Methods (B), (C) and (D) are applied when substituent A of formula (I) is different from a bond σ.

Method (A):

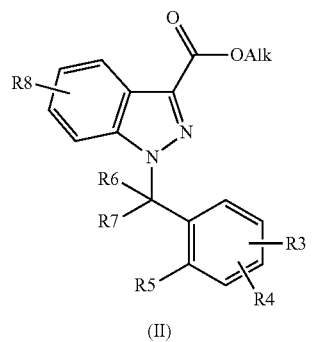

(II)

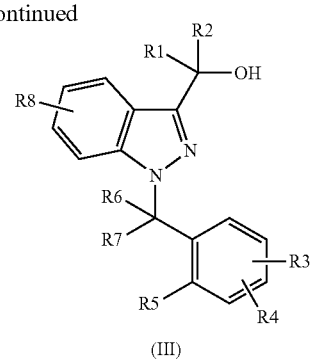

(III)

In method (A), the esters of indazolcarboxylic acid of general formula (II), in which Alk indicates an alkyl group containing from 1 to 5 carbon atoms, are reduced to the respective alcohols of general formula (III). The substituents $R_1$ to $R_8$ have the meanings given previously for the compounds of formula (I).

Method (A) may be performed according to conventional methods.

For example, the reduction of the carboxylic esters of formula (II) may be performed with the aid of reducing reagents such as lithium aluminium hydride, sodium borohydride or organometallic agents such as Grignard reagents. In general, the reaction is performed in a suitable aprotic solvent such as, for example, tetrahydrofuran, diethyl ether and 1,4-dioxane.

The reactions are generally performed at a temperature that may vary from about 0° C. to the reflux temperature of the solvent, while they may last from 1-2 hours to 24 hours.

Mehod (B):

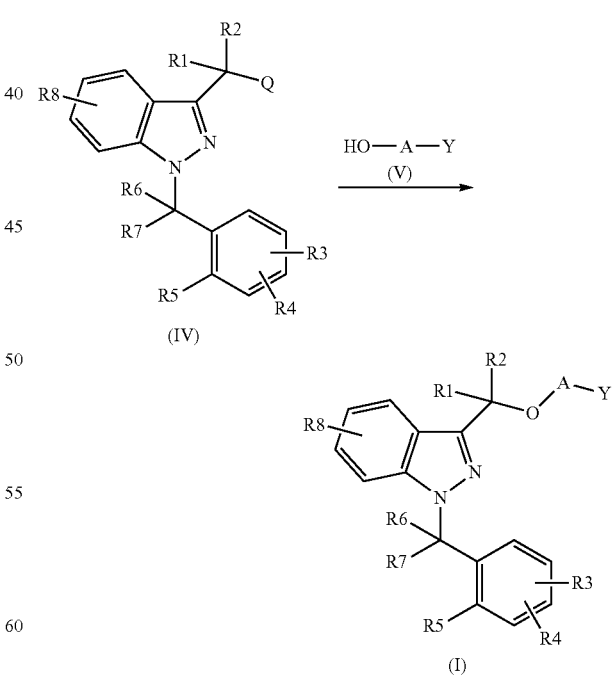

In method (B), the products of general formula (IV), in which Q indicates a leaving group chosen from the group comprising halogen, $CH_3SO_3$— and p-$CH_3PhSO_3$—, are reacted with the alcohols of general formula (V). The substituents $R_1$ to $R_8$, A and Y have the meanings given previously for the compounds of formula (I).

Method (B) may be performed according to conventional techniques.

For example, the alcohols of formula (V) are reacted with the derivatives of formula (IV). Preferably, Q is a leaving group chosen from the group comprising a chlorine atom, a bromine atom and a methanesulfonyl group.

The reaction is performed in the presence of a suitable base and in a suitable solvent. The bases that may be used are NaH, butyllithium and lithium diisopropylamide, whereas the solvents that are suitable for this type of reaction are generally polar aprotic solvents such as, for example, tetrahydrofuran, diethyl ether and 1,4-dioxane. Generally, the reaction is performed at a temperature between room temperature and the reflux temperature of the solvent used. Reactions of this type may last from a few hours to a few days.

Mehod (C):

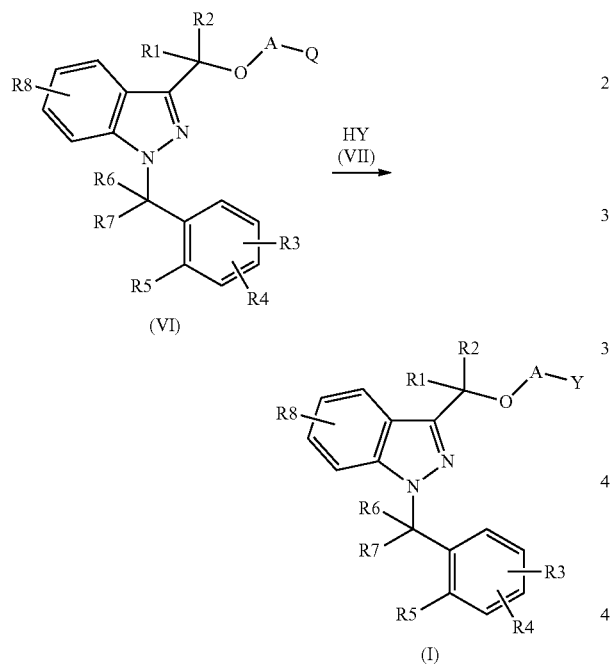

In method (C), the products of general formula (VI), in which Q indicates a leaving group chosen from the group comprising halogen, $CH_3SO_3$— and p-$CH_3PhSO_3$—, are reacted with the alcohols and amines of general formula (VII). The substituents $R_1$ to $R_8$, A and Y have the meanings given previously for the compounds of formula (I).

Method (C) may be performed according to conventional techniques.

For example, the amines of general formula (VII) are reacted with the derivatives of formula (VI) in the presence of a suitable base and in a suitable solvent. Preferably, Q is a leaving group preferably chosen from the group comprising a chlorine atom, a bromine atom and a methanesulfonyl group. The bases preferably used are sodium carbonate, potassium carbonate, and aliphatic amines such as triethylamine, diisopropylethylamine or the same reactive amine (VII). Preferably, the solvents used are polar aprotic solvents such as N,N-dimethylformamide, tetrahydrofuran and dichloromethane. In general, the reaction is performed at a temperature between room temperature and the reflux point of the solvent used. Reactions of this type may last from a few hours to a few days.

When the compounds of formula (VII) are alcohols, the standard reaction techniques may use a strong base such as NaH, butyllithium or lithium diisopropylamide, and suitable polar aprotic solvents such as tetrahydrofuran, diethyl ether or 1,4-dioxane. In general, the reaction is performed at a temperature between room temperature and the reflux point of the solvent used. Reactions of this type may last from a few hours to a few days.

Method (D):

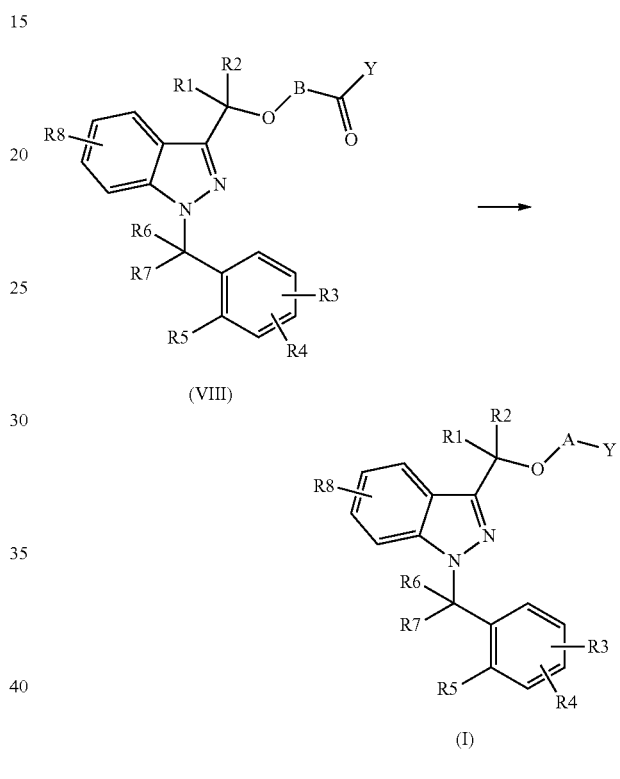

In method (D), the esters or amides of general formula (VIII) are reduced, respectively, to the alcohols or amines of general formula (I). The substituents $R_1$ to $R_8$, A and Y have the meanings given previously for the compounds of formula (I), and in which the group B—$CH_2$ has the same meaning as A.

Method (D) may be performed according to the standard methods.

For example, the reduction of the carbonyl compounds of formula (VIII) may be performed with the aid of reducing reagents such as lithium aluminium hydride, sodium borohydride or organometallic agents such as Grignard reagents. In general, the reaction is performed in suitable aprotic solvents, for instance tetrahydrofuran, diethyl ether and 1,4-dioxane.

The reactions are generally performed at a temperature that may range from about 0° C. to the reflux point of the solvent, while the reaction time may range from 1-2 hours to 24 hours.

The examples that follow are intended to illustrate the present invention without, however, limiting it in any way.

PREPARATIVE EXAMPLES

The compounds of formula (I) listed in Table A below were prepared using the preparation methods previously described.

TABLE A

| No. | A | Y | R1 | R2 | R3 | R4 | R5 | R6 | R7 | R8 |
|---|---|---|---|---|---|---|---|---|---|---|
| 1 | σ | H | H | H | H | H | H | H | H | H |
| 2 | " | " | " | " | p-OCH$_3$ | " | " | " | " | " |
| 3 | " | " | " | " | p-CH$_3$ | " | " | " | " | " |
| 4 | " | " | " | " | p-Cl | " | " | " | " | " |
| 5 | " | " | " | " | m-Cl | p-Cl | " | " | " | " |
| 6 | " | " | " | " | o-Cl | p-Cl | " | " | " | " |
| 7 | " | " | " | " | p-F | H | " | " | " | " |
| 8 | " | " | " | " | o-CH$_3$ | p-Cl | " | " | " | " |
| 9 | " | " | " | " | H | H | " | " | " | 5-OCH$_3$ |
| 10 | " | " | CH$_3$ | CH$_3$ | o-CH$_3$ | p-Cl | " | " | " | H |
| 11 | " | " | " | " | o-Cl | " | " | " | " | " |
| 12 | " | " | CH$_3$ | H | o-CH$_3$ | " | " | " | " | " |
| 13 | CH$_2$CH$_2$ | OH | H | " | H | H | " | " | " | " |
| 14 | " | N(CH$_3$)$_2$ | " | " | " | " | " | " | " | " |
| 15 | CH$_2$CH$_2$CH$_2$ | " | " | " | " | " | " | " | " | " |
| 16 | " | OH | " | " | " | " | " | " | " | " |
| 17 | C(CH$_3$)$_2$CH$_2$ | " | " | " | " | " | " | " | " | " |
| 18 | " | N-morpholine | " | " | " | " | " | " | " | " |
| 19 | (CH$_2$)$_2$ | OH | CH$_3$ | CH$_3$ | " | " | " | CH$_3$ | CH$_3$ | " |
| 20 | " | " | H | H | p-CF$_3$ | " | " | H | H | 5-CN |
| 21 | " | " | " | " | p-N(CH$_3$)$_2$ | " | " | " | " | 5-Cl |
| 22 | " | " | " | " | p-Cl | o-Cl | o'-CH$_3$ | " | " | " |
| 23 | " | N(CH$_3$)$_2$ | " | " | H | H | H | " | CO | " |
| 24 | " | " | " | " | " | " | " | H | H | 5-CONH$_2$ |
| 25 | " | " | " | " | " | " | (CH$_2$)$_3$ | | | 5-NO$_2$ |
| 26 | " | " | " | " | o-N(CH$_3$)$_2$ | " | H | H | " | H |
| 27 | " | " | " | " | m-OH | " | " | " | CO | " |
| 28 | (CH$_2$)$_2$OCH$_2$ | H | " | " | H | " | " | H | H | H |
| 29 | " | " | CH$_3$ | CH$_3$ | " | " | " | " | " | 5-Cl |
| 30 | " | " | H | H | p-OCH$_3$ | " | " | CH$_3$ | CH$_3$ | H |
| 31 | " | " | " | " | H | " | (CH$_2$)$_3$ | | H | " |
| 32 | (CH$_2$)$_2$O(CH$_2$)$_2$ | N(CH$_3$)$_2$ | " | " | o-OCH$_3$ | " | H | H | " | " |
| 33 | " | " | " | " | p-OCH$_3$ | o-CH$_3$ | o'-CH$_3$ | " | " | " |
| 34 | C(CH$_3$)$_2$CH$_2$OCH$_2$ | H | " | " | m-NO$_2$ | H | H | " | " | 5-NO$_2$ |
| 35 | C(CH$_3$)$_2$CH$_2$ | NHCH$_2$CH$_3$ | CH$_3$ | CH$_3$ | H | " | " | " | " | H |
| 36 | " | NH-2-pyridine | H | H | " | " | " | " | CO | " |
| 37 | C(CH$_3$)$_2$CH$_2$O(CH$_2$)$_2$ | N(CH$_3$)$_2$ | " | " | p-CH$_3$ | o-CH$_3$ | o'-CH$_3$ | H | H | " |
| 38 | σ | OH | " | " | H | H | H | " | " | 5-CN |
| 39 | " | " | " | " | " | " | " | " | " | 5-CONH$_2$ |

The details of the preparation of compounds 1 to 18 are given hereinbelow. Compounds 19 to 39 were prepared with similar techniques using suitable starting products and reagents.

Preparation of Compound 1

1-benzyl-3-hydroxymethyl-indazole

The preparation of product 1 was performed as described in Example 1a of EP 0382 276 A2.

Preparation of Compound 2

[1-(4-methoxybenzyl)-1H-indazol-3-yl]methanol

To a suspension of 60% NaH (2.7 g; 0.07 mol) in toluene (200 ml) was added 1-benzyl-3-hydroxymethylindazole (10 g; 0.07 mol). The mixture was brought to boiling point and left stirring at reflux for 1 hour. 4-Methoxybenzyl chloride (14 g; 0.09 mol) was then added. The mixture was then stirred at reflux for 4 hours. The reaction was completed by cooling the mixture to room temperature and adding water (50 ml). The organic phase was separated out and washed, respectively, with 2N HCl (50 ml) and water (5×50 ml). The solvent was evaporated off under reduced pressure. The crude residue thus obtained was purified by flash chromatography on silica gel, using as eluent a 3/2 hexane/ethyl acetate mixture. The product obtained was crystallized from a 5/1 hexane/ethyl acetate mixture to give 5.1 g of [1-(4-methoxybenzyl)-1H-indazol-3-yl]methanol with a melting point of 95°-97° C.

$^1$H-NMR (CDCl$_3$, δ ppm): 3.43 (t, J=6.9 Hz, 1 H), 3.67 (s, 3 H), 4.98 (d, J=6.9 Hz, 2 H), 5.36 (s, 2 H), 6.5-6.8 (m, 2 H), 6.9-7.4 (m, 7 H), 7.80 (d, J=7.86 Hz, 1 H).

Preparation of Compound 3

[1-(4-methylbenzyl)-1H-indazol-3-yl]methanol

The product was obtained using the method described for the preparation of compound 2, but using as reagent 4-methylbenzyl chloride (0.09 mol) instead of 4-methoxybenzyl chloride.

The product obtained was purified by crystallization from a 5/1 hexane/ethyl acetate mixture.

m.p.=90°-92° C.

$^1$H-NMR (CDCl$_3$, δ ppm): 2.24 (s, 3 H), 3.4 (bs, 1 H), 5.0 (s, 2 H), 5.36 (s, 2 H), 6.9-7.4 (m, 7 H), 7.79 (d, J=7.84 Hz, 1 H).

Preparation of Compound 4

[1-(4-chlorobenzyl)-1H-indazol-3-yl]methanol

The product was obtained using the method described for the preparation of compound 2 but using 4-chlorobenzyl chloride as reagent (0.09 mol) instead of 4-methoxybenzyl chloride.

The product obtained was purified by crystallization from a 5/1 hexane/ethyl acetate mixture.

m.p.=102°-104° C.

$^1$H-NMR (CDCl$_3$, δ ppm): 3.5 (bs, 1 H), 5.01 (s, 2 H), 5.37 (s, 2 H), 6.8-7.5 (m, 7 H), 7.81 (d, J=7.82 Hz, 1 H).

Preparation of Compound 5

[1-(3,4-dichlorobenzyl)-1H-indazol-3-yl]methanol

The product was obtained using the method described for the preparation of compound 2, but using as reagent 3,4-dichlorobenzyl chloride (0.09 mol) instead of 4-methoxybenzyl chloride.

The product obtained was purified by crystallization from a 1/1 hexane/ethyl acetate mixture.

m.p.=118°-120° C.

$^1$H-NMR (CDCl$_3$, δ ppm): 3.1-3.3 (m, 1 H), 4.9-5.2 (m, 2 H), 5.38 (s, 2 H), 6.89 (dd, J=8.27; 2.05 Hz, 1 H), 7.1-7.5 (m, 5 H), 7.82 (dt, J=8.01; 0.93, 1 H).

Preparation of Compound 6

[1-(2,4-dichlorobenzyl)-1H-indazol-3-yl]methanol

The product was obtained using the method described for the preparation of compound 2, but using as reagent 2,4-dichlorobenzyl chloride (0.09 mol) instead of 4-methoxybenzyl chloride.

The product obtained was purified by crystallization from a 7/3 ethanol/water mixture.

m.p.=105°-106° C.

$^1$H-NMR (CDCl$_3$, δ ppm): 3.0 (bs, 1 H), 5.04 (s, 2 H), 5.52 (s, 2 H), 6.58 (d, J=8.36 Hz, 1 H), 6.96 (dd, J=8.34; 2.07 Hz, 1 H), 7.1-7.5 (m, 4 H), 7.84 (dt, J=9.79; 1.12 Hz, 1 H).

Preparation of Compound 7

[1-(4-fluorobenzyl)-1H-indazol-3-yl]methanol

The product was obtained using the method described for the preparation of compound 2, but using as reagent 4-fluorobenzyl chloride (0.09 mol) instead of 4-methoxybenzyl chloride.

The product was purified by crystallization from hexane.

m.p.=80°-81° C.

$^1$H-NMR (CDCl$_3$, δ ppm): 3.4 (bs, 1 H), 5.02 (s, 2 H), 5.38 (s, 2 H), 6.7-7.5 (m, 7 H), 7.83 (d, J=8.01 Hz, 1 H).

Preparation of Compound 8

[1-(4-chloro-2-methylbenzyl)-1H-indazol-3-yl] methanol

The product was obtained using the method described for the preparation of compound 2, but using as reagent 4-chloro-2-methylbenzyl chloride (0.09 mol) instead of 4-methoxybenzyl chloride.

The product was purified by crystallization from absolute ethanol.

m.p.=109°-110° C.

$^1$H-NMR (DMSO-d6, δ ppm): 2.34 (s, 3 H), 4.78 (d, J=5.70 Hz, 2 H), 5.26 (td, J=5.77; 0.88 Hz, 1 H), 5.58 (s, 2 H), 6.74 (d, J=8.18 Hz, 1 H), 7.09-7.18 (m, 2 H), 7.29 (d, J=2.05 Hz, 1 H), 7.37 (ddd, J=8.33; 7.02; 1.02 Hz, 1 H), 7.59 (d, J=8.48 Hz, 1 H), 7.88 (d, J=8.04 Hz, 1 H).

Preparation of Compound 9

(1-benzyl-5-methoxy-1H-indazol-3-yl)methanol 9a) benzyl 1-benzyl-5-methoxy-1H-indazole-3-carboxylate A suspension of 5-methoxy-1H-indazole-3-carboxylic acid (21.5 g; 0.11 mol) and 60% NaH (10.5 g; 0.44 mol) in N,N-dimethylformamide (DMF) (200 ml) was stirred at 70° C. for 1 hour. Benzyl chloride (32.9 g; 0.26 mol) was then added slowly and the mixture was stirred at 70° C. for 4 hours. The reaction was completed by cooling the mixture to room temperature and pouring the mixture into water and ice. The product was extracted with ethyl acetate (3×250 ml). The combined organic phases were concentrated under reduced pressure. The crude residue thus obtained was purified by successive crystallizations from 95° ethanol, to give 18 g of benzyl 1-benzyl-5-methoxy-1H-indazole-3-carboxylate with a melting point of 107-109° C.

$^1$H-NMR (CDCl$_3$, δ ppm): 3.78 (s, 3 H), 5.51 (s, 2 H), 6.9-7.6 (m, 13 H).

9b) (1-benzyl-5-methoxy-1H-indazol-3-yl)methanol

To a solution of benzyl 1-benzyl-5-methoxy-1H-indazole-3-carboxylate (17.7 g; 0.05 mol), diethyl ether (100 ml) and tetrahydrofuran (THF) (170 ml) stirred at room temperature was slowly added LiAlH$_4$ (3.8 g; 0.1 mol). Once the addition was complete, the suspension was stirred at reflux for 24 hours. The reaction was completed by destroying the excess LiAlH$_4$ via addition of water (40 ml) and 5N NaOH (10 ml). The organic phase was separated out and the solvent was evaporated off under reduced pressure. The crude residue obtained was purified by crystallization from 95° ethanol, to give 14 g of (1-benzyl-5-methoxy-1H-indazol-3-yl)methanol with a melting point of 97°-98° C.

$^1$H-NMR (CDCl$_3$, δ ppm): 3.3 (bs, 1 H), 3.80 (s, 3 H), 4.92 (s, 2 H), 5.47 (s, 2 H), 6.9-7.5 (m, 8 H).

Preparation of Compound 10

2-[1-(4-chloro-2-methylbenzyl)-1H-indazol-3-yl] propan-2-ol 10a) ethyl 1-(4-chloro-2-methylbenzyl)-1H-indazole-3-carboxylate To a suspension of 1-(4-chloro-2-methylbenzyl)-1H-indazole-3-carboxylic acid, prepared as described in *J. Med. Chem.* (1976) 19, 778-783, (120 g; 0.4 mol) in absolute ethanol (850 ml), stirred at room temperature, was cautiously added concentrated H$_2$SO$_4$ (15 ml). The mixture was then refluxed for 9 hours. The reaction was then completed by cooling the mixture to room temperature. The solid thus formed was filtered off under cold conditions (10° C.) and washed thoroughly on the filter with water. 126 g of ethyl 1-(4-chloro-2-methylbenzyl)-1H-indazole-3-carboxylate were thus obtained, and were used in the following reaction without further purification.

m.p.=120°-122° C.

$^1$H-NMR (CDCl$_3$, δ ppm): 1.49 (t, J=7.21 Hz, 3 H), 2.33 (s, 3 H), 4.53 (q, J=7.21 Hz, 2 H), 5.85 (s, 2 H), 6.67 (d, J=8.20 Hz, 1 H), 7.0-7.4 (m, 5 H), 8.1-8.3 (m, 1 H).

10b) 2-[1-(4-chloro-2-methylbenzyl)-1H-indazol-3-yl]propan-2-ol

To a solution formed from magnesium shavings (2.4 g; 0.1 mol) and methyl iodide (6.1 ml; 0.1 mol) in diethyl ether (100 ml), stirred at about 5° C., was added ethyl 1-(4-chloro-2-methylbenzyl)-1H-indazole-3-carboxylate (13.2 g; 0.04 mol). The mixture was stirred under cold conditions for 24 hours. The reaction was completed by adding saturated ammonium chloride solution (50 ml) and the organic phase separated out was washed with water (2×50 ml). The organic phase was then concentrated under reduced pressure and the crude residue was purified by crystallization from 40-60° C. petroleum ether.

6 g of 2-[1-(4-chloro-2-methylbenzyl)-1H-indazol-3-yl]propan-2-ol were thus obtained.

m.p.=72°-74° C.

$^1$H-NMR (DMSO-d6, δ ppm): 1.60 (s, 6 H), 2.38 (s, 3 H), 5.24 (s, 1 H), 5.56 (s, 2 H), 6.66 (d, J=8.18 Hz, 1 H), 7.04-7.16 (m, 2 H), 7.25-7.36 (m, 2 H), 7.52 (d, J=8.48 Hz, 1 H), 8.05 (d, J=8.33 Hz, 1 H).

Preparation of Compound 11

2-[1-(2,4-dichlorobenzyl)-1H-indazol-3-yl]propan-2-ol 11a) ethyl 1-(2,4-dichlorobenzyl)-1H-indazole-3-carboxylate The product was obtained using the method described for the preparation of compound 10a, but using as reagent 1-(2,4-dichlorobenzyl)-1H-indazole-3-carboxylic acid, prepared as described in *J. Med. Chem.* (1976) 19, 778-783, (0.4 mol) instead of 1-(4-chloro-2-methylbenzyl)-1H-indazole-3-carboxylic acid.

The product was purified by flash chromatography on silica gel, using a 7/3 hexane/ethyl acetate mixture as eluent.

$^1$H-NMR (CDCl$_3$, δ ppm): 1.47 (t, J=7.24 Hz, 3 H), 5.42 (q, J=7.24 Hz, 2 H), 5.75 (s, 2 H), 6.68 (d, J=8.75 Hz, 1 H), 6.9-7.5 (m, 5 H), 8.1-8.4 (m, 1 H).

11b) 2-[1-(2,4-dichlorobenzyl)-1H-indazol-3-yl]propan-2-ol

The product was obtained using the method described for the preparation of compound 10b, but using as starting material compound 11a (0.4 mol) instead of compound 10a.

The product was purified by twofold crystallization from hexane.

m.p.=76°-78° C.

$^1$H-NMR (DMSO-d6, δ ppm): 1.60 (s, 6 H), 5.26 (s, 1 H), 5.65 (s, 2 H), 6.72 (d, J=8.33 Hz, 1 H), 7.11 (t, J=7.45 Hz, 1 H), 7.27-7.40 (m, 2 H), 7.54 (d, J=8.48 Hz, 1 H), 7.66 (d, J=2.19 Hz, 1 H), 8.07 (d, J=8.18 Hz, 1 H).

Preparation of Compound 12

1-[1-(4-chloro-2-methylbenzyl)-1H-indazol-3-yl]ethanol 12a) 1-(4-chloro-2-methylbenzyl)-1H-indazole-3-carboxaldehyde The mixture formed from 1-(4-chloro-2-methylbenzyl)-1H-indazole-3-carboxylic acid (250 g; 0.83 mol) and thionyl chloride (450 ml) was stirred at 50° C. until dissolution of the starting material was complete (30 minutes), and was then heated at 80° C. for 5 hours. The reaction was completed by cooling the solution to room temperature and removing the solvent by distillation under reduced pressure. The residue was then treated with hexane (300 ml) and the solid thus formed was filtered off and dried under vacuum to give 240 g of the intermediate acyl chloride, which product was suspended in toluene (2.5 L) and N-methylaniline (88 g; 0.82 mol) was added thereto at room temperature. The mixture was then stirred at 80° C. for 6 hours. The reaction was then completed by adding toluene (1.5 L) to the mixture and washing the solution with water until neutral. The organic phase was concentrated to 50% under reduced pressure. The solution was then cooled to 0° C. and the solid obtained was filtered off, to give about 230 g of aniline, which product was dissolved in diethyl ether (2.7 L) and THF (400 ml). The solution obtained was stirred at 0° C. LiAlH$_4$ (10.8 g; 0.29 mol) was slowly added to the solution. Once the addition was complete, the suspension was stirred at room temperature for 24 hours. The reaction was completed by cautiously adding to the mixture water (20 ml), 2N NaOH (20 ml) and again water (35 ml). The mixture was then filtered and the solvent was concentrated under reduced pressure. The residue was taken up in methanol (3.5 L) and stirred at 50° C. To this solution was added a solution of NaHSO$_3$ (228 g; 2.19 mol) in water (650 ml). The mixture was stirred for 30 minutes and then cooled to 0° C., and the solid thus formed was filtered off and then added to an aqueous 10% Na$_2$CO$_3$ solution (3 L) stirred at room temperature. After 3 hours, the mixture was filtered and the solid was purified by crystallization first from a 1/1 ethanol/ethyl acetate mixture and then from 95° ethanol.

98 g of 1-(4-chloro-2-methylbenzyl)-1H-indazole-3-carboxaldehyde were thus obtained.

m.p.=107°-109° C.

$^1$H-NMR (DMSO-d6, δ ppm): 2.35 (s, 3 H), 5.84 (s, 2 H), 6.91 (d, J=8.73 Hz, 1 H), 7.1-8.3 (m, 6 H), 10.18 (s, 1 H).

12b) 1-[1-(4-chloro-2-methylbenzyl)-1H-indazol-3-yl]ethanol

The product was obtained using the method described for the preparation of compound 10b, but using as starting material compound 12a (0.4 mol) instead of compound 10a.

The product was purified by crystallization from hexane.

m.p.=82°-84° C.

$^1$H-NMR (DMSO-d6, δ ppm): 1.54 (d, J=6.58 Hz, 3 H), 2.36 (s, 3 H), 5.10 (dq, J=6.53; 4.82 Hz, 1 H), 5.34 (d, J=4.82 Hz, 1 H), 5.56 (s, 2 H), 6.70 (d, J=8.18 Hz, 1 H), 7.06-7.17 (m, 2 H), 7.29 (d, J=1.90 Hz, 1 H), 7.34 (ddd, J=8.33; 7.02; 1.02 Hz, 1 H), 7.56 (d, J=8.48 Hz, 1 H), 7.95 (d, J=8.18 Hz, 1 H).

Preparation of Compound 13

2-[(1-benzyl-1H-indazol-3-yl)methoxy]ethanol

To a solution of NaOH (2.8 g; 0.07 mol) in ethylene glycol (150 ml) stirred at room temperature was added 1-benzyl-3-chloromethylindazole, prepared as described in Example 2a of EP 382 276 (17.6 g; 0.07 mol). The solution was heated at 130° C. for 4 hours and then cooled to room temperature, and the solvent was evaporated off under reduced pressure. The residue was taken up in water (100 ml) and the product was extracted with ethyl acetate (3×100 ml). The combined organic phases were concentrated under reduced pressure and the crude residue obtained was purified by crystallization from an approximately 1/1 hexane/ethyl acetate mixture.

13.8 g of 2-[(1-benzyl-1H-indazol-3-yl)methoxy]ethanol were thus obtained.

m.p.=67°-69° C.

$^1$H-NMR (CDCl$_3$, δ ppm): 2.15 (bs, 1 H), 3.61-3.82 (m, 4 H), 4.97 (s, 2 H), 5.57 (s, 2 H), 7.11-7.38 (m, 8 H), 7.81 (dt, J=8.15; 0.97 Hz, 1 H).

Preparation of Compound 14

2-[(1-benzyl-1H-indazol-3-yl)methoxy]-N,N-dimethylethanamine hydrochloride

To a solution of (1-benzyl-1H-indazol-3-yl)methanol (20 g; 0.084 mol) in toluene (200 ml) stirred at room temperature was added 55% NaH (3.6 g; 0.082 mol). 30 minutes after the end of addition, a solution of 2-chloro-N,N-dimethylethanamine (9.2 g; 0.082 mol) in toluene (200 ml) was added. The mixture was stirred at reflux for 7 hours. The reaction was completed by adding water (200 ml). The organic phase was washed with water (3×100 ml) and then extracted with dilute $H_2SO_4$ (3×100 ml). The combined acidic phases were washed with toluene (3×50 ml) and were then brought to basic pH with 10 N NaOH. The product was then extracted with ethyl acetate (3×200 ml) and the combined organic phases were washed with water until neutral. The solvent was then concentrated under reduced pressure and the crude residue obtained was purified by distillation at a pressure of 0.4 mmHg and at 182°-185° C.

16 g of 2-[(1-benzyl-1H-indazol-3-yl)methoxy]-N,N-dimethyl-ethanamine (oil) were thus obtained.

A portion of this product (13.1 g; 0.042 mol) was dissolved in isobutanol (150 ml) and treated with concentrated HCl (3.5 ml; 0.045 mol) at room temperature for 1 hour. After treatment, the solvent was evaporated off under reduced pressure. The solid product thus obtained was purified by crystallization from isopropanol.

10 g of 2-[(1-benzyl-1H-indazol-3-yl)methoxy]-N,N-dimethyl-ethanamine hydrochloride were thus obtained.

m.p.=138°-140° C.

$^1$H-NMR (DMSO-d6, δ ppm): 2.72 (s, 6 H), 3.28 (t, J=5.10 Hz, 2 H), 3.85 (t, J=5.10 Hz, 2 H), 4.88 (s, 2 H), 5.65 (s, 2 H), 7.17 (ddd, J=7.97; 7.06; 0.66 Hz, 1 H), 7.21-7.35 (m, 5 H), 7.41 (ddd, J=8.38; 6.98; 0.99 Hz, 1 H), 7.72 (d, J=8.42 Hz, 1 H), 7.88 (d, J=8.09 Hz, 1 H), 10.68 (bs, 1 H).

Preparation of Compound 15

3-[(1-benzyl-1H-indazol-3-yl)methoxy]-N,N-dimethylpropan-1-amine hydrochloride

The product was obtained using the method described for the preparation of compound 14, but using as reagent 3-chloro-N,N-dimethylpropan-1-amine (0.08 mol) instead of 2-chloro-N,N-dimethylethanamine.

The product was purified by twofold crystallization from isopropanol.

m.p.=119°-121° C.

$^1$H-NMR (DMSO-d6, δ ppm): 1.86-2.02 (m, 2 H), 2.68 (s, 6 H), 2.99-3.09 (m, 2 H), 3.55 (t, J=6.03 Hz, 2 H), 4.81 (s, 2 H), 5.63 (s, 2 H), 7.16 (ddd, J=7.97; 6.98; 0.74 Hz, 1 H), 7.20-7.34 (m, 5 H), 7.39 (ddd, J=8.34; 7.02; 0.99 Hz, 1 H), 7.69 (d, J=8.59 Hz, 1 H), 7.83 (dt, J=8.13; 0.89 Hz, 1 H), 10.75 (bs, 1 H).

Preparation of Compound 16

3-[(1-benzyl-1H-indazol-3-yl)methoxy]propan-1-ol

The product was obtained using the method described for the preparation of compound 13, but using as reagent 1,3-propanediol (150 ml) instead of ethylene glycol.

The product was purified by flash chromatography on silica gel, using as eluent a 1/1 hexane/ethyl acetate mixture.

$^1$H-NMR (CDCl$_3$, δ ppm): 1.85 (q, J=5.83 Hz, 2 H), 2.75 (bs, 1 H), 3.71 (t, J=7.74 Hz, 4 H), 4.91 (s, 2 H), 5.55 (s, 2 H), 7.0-7.4 (m, 8 H), 7.80 (d, J=7.77 Hz, 1 H).

Preparation of Compound 17

2-[(1-benzyl-1H-indazol-3-yl)methoxy]-2-methyl-propan-1-ol

To a suspension of LiAlH$_4$ (4.48 g; 0.118 mol) in diethyl ether (100 ml) stirred at room temperature was slowly added a solution of methyl 2-[(1-benzyl-1H-indazol-3-yl)methoxy]-2-methylpropanoate, prepared according to the method described in EP 0 382 276, (20 g; 0.06 mol) in diethyl ether (200 ml) and THF (50 ml). Once the addition was complete, the mixture was stirred at room temperature for 30 minutes and the reaction was then completed by adding 10 N NaOH (20 ml) and water (40 ml). The solvent was evaporated off under reduced pressure and the oily residue was purified by distillation at 0.01 mmHg at 190° C. The solid product thus obtained was crystallized from isopropanol.

11 g of 2-[(1-benzyl-1H-indazol-3-yl)methoxy]-2-methylpropan-1-ol were thus obtained.

m.p.=52°-53° C.

$^1$H-NMR (CDCl$_3$, δ ppm): 1.34 (s, 6 H), 2.50 (bs, 1 H), 3.51 (s, 2 H), 4.87 (s, 2 H), 5.55 (s, 2 H), 7.14 (ddd, J=8.04; 6.21; 1.68 Hz, 1 H), 7.17-7.38 (m, 7 H), 7.78 (dt, J=8.08; 1.00 Hz, 1 H).

Preparation of Compound 18

1-benzyl-3-[(1,1-dimethyl-2-morpholin-4-ylethoxy)methyl]-1H-indazole maleate 18a) 1-benzyl-3-[(1,1-dimethyl-2-morpholin-4-yl-2-oxyethoxy)methyl]-1H-indazole 72 g (0.222 mol) of 2-[(1-benzyl-1H-indazol-3-yl)methoxy]-2-methyl-propanoic acid were treated at room temperature with 30% sodium methoxide in methanol (39 ml; 0.222 mol) for 10 minutes, and the solvent was then evaporated off under reduced pressure and the residue obtained was suspended in anhydrous toluene (750 ml). To the suspension, stirred at room temperature, was added morpholine (77.6 ml; 0.888 mol) followed by slow addition of a solution of thionyl chloride (19.3 ml; 0.266 mol) in toluene (150 ml). The mixture was stirred for 24 hours and the reaction was then completed by filtering off the solid thus formed. The solution was concentrated under reduced pressure and the crude residue obtained was purified by crystallization from isopropanol.

14 g of 1-benzyl-3-[(1,1-dimethyl-2-morpholin-4-yl-2-oxyethoxy)methyl]-1H-indazole were obtained.

$^1$H-NMR (DMSO-d6, δ ppm): 1.47 (s, 6 H), 3.1-4.0 (2bs, 8 H), 4.73 (s, 2 H), 5.83 (s, 2 H), 7.0-7.9 (m, 9 H).

18b) 1-benzyl-3-[(1,1-dimethyl-2-morpholin-4-ylethoxy)methyl]-1H-indazole maleate To a suspension of LiAlH$_4$ (5.16 g; 0.136 mol) in diethyl ether (100 ml) stirred at room temperature was added a solution of 1-benzyl-3-[(1,1-dimethyl-2-morpholin-4-yl-2-oxyethoxy)methyl]-1H-indazole (27 g; 0.068 mol) in THF (180 ml). The mixture was then refluxed for 1 hour. After refluxing, the reaction was completed by adding 10 N NaOH (25 ml) and water (50 ml). The organic phase was then separated out and extracted with 1N HCl (2×50 ml). The combined acidic phases were brought to basic pH with 1N NaOH and then extracted with diethyl ether (3×150 ml). The combined organic phases were concentrated under reduced pressure and the crude residue was purified by crystallization from isopropanol, to give 6 g of 1-benzyl-3-[(1,1-dimethyl-2-morpholin-4-ylethoxy)methyl]-1H-indazole.

The 1-benzyl-3-[(1,1-dimethyl-2-morpholin-4-ylethoxy) methyl]-1H-indazole was then dissolved in absolute ethanol (50 ml) and treated at room temperature with maleic acid (1.75 g; 0.016 mol). The solid obtained was filtered off and purified by crystallization from isopropanol.

5.4 g of 1-benzyl-3-[(1,1-dimethyl-2-morpholin-4-ylethoxy)methyl]-1H-indazole maleate were thus obtained. m.p.=87°-88° C.

$^1$H-NMR (DMSO-d6, δ ppm): 1.38 (s, 6 H), 3.09 (bs, 8 H), 3.71 (bs, 4 H), 4.80 (s, 2 H), 5.61 (s, 2 H), 6.09 (s, 2 H), 7.09-7.44 (m, 7 H), 7.70 (d, J=8.59 Hz, 1 H), 7.82 (d, J=8.09 Hz, 1 H).

Example 1

Analysis of the Gene Expression of MCP-1 in a Human Monocyte Line

The capacity of the compounds to inhibit the expression of MCP-1 by lipopolysaccharide (LPS)-stimulated MonoMac6 cells was evaluated. The cells were placed in 96-well plates at a concentration of 50 000 cells/well. The compounds were tested at the maximum soluble concentration given in Table 1 (in the range 30-300 μM) and incubated for 1 hour. The cells were then stimulated with LPS (100 ng/ml) for 4 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human MCP-1 was used (Applied Biosystems, RefSeq NM_002982.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 1 below.

TABLE 1

| No. | % inhibition | [μM] |
| --- | --- | --- |
| 1 | 30 | 150 |
| 10 | 72 | 30 |
| 14 | 52 | 150 |
| 13 | 55 | 300 |
| 17 | 53 | 150 |

As shown by the results obtained and given in Table 1, the compounds were capable of significantly inhibiting the LPS-induced expression of MCP-1 in a human monocyte line, and showed a reduction in the levels of specific mRNA between 30% and 72%.

Example 2

Measurement of the Production of MCP-1 in a Human Monocyte Line

The capacity of the compounds to inhibit the expression of the protein MCP-1 by lipopolysaccharide (LPS)-stimulated MonoMac6 cells was evaluated. The cells were placed in 96-well plates at a concentration of 50 000 cells/well. The compounds were tested at the maximum soluble concentration given in Table 2 (in the range 30-300 μM) and incubated for 1 hour. The cells were then stimulated with LPS (100 ng/ml) for 20 hours.

The amount of MCP-1 produced was measured in the supernatants, suitably diluted with buffer, by means of an immunoenzymatic test (ELISA) using a commercial kit (ELISA MCP-1/JE, R&D Systems).

The results obtained, expressed as a percentage of inhibition, are collated in Table 2 below.

TABLE 2

| No. | % inhibition | [μM] |
| --- | --- | --- |
| 1 | 54 | 150 |
| 4 | 85 | 75 |
| 6 | 54 | 30 |
| 8 | 75 | 30 |
| 10 | 81 | 30 |
| 11 | 88 | 30 |
| 12 | 76 | 30 |
| 13 | 78 | 300 |
| 14 | 64 | 150 |
| 15 | 44 | 75 |
| 17 | 82 | 150 |
| 18 | 85 | 75 |

As shown by the results obtained and given in Table 2, the compounds were capable of significantly inhibiting the LPS-induced expression of MCP-1 in a human monocyte line, and showed a reduction in the levels of produced protein of between 44% and 88%.

Example 3

Analysis of the Gene Expression of CX3CR1 in a Human Monocyte Line

The capacity of the compounds to inhibit the expression of CX3CR1 by lipopolysaccharide (LPS)-stimulated MonoMac6 cells was evaluated. The cells were placed in 96-well plates at a concentration of 50 000 cells/well. The compounds were tested at the maximum soluble concentration given in Table 3 (in the range 30-300 μM) and incubated for 1 hour. The cells were then stimulated with LPS (100 ng/ml) for 20 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human CX3CR1 was used (Applied Biosystems, RefSeq NM_001337.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 3 below.

TABLE 3

| No. | % inhibition | [µM] |
|---|---|---|
| 1 | 72 | 150 |
| 10 | 89 | 30 |
| 13 | 90 | 300 |
| 14 | 96 | 150 |
| 17 | 88 | 150 |

As shown by the results obtained and given in Table 3, the compounds were capable of significantly inhibiting the LPS-induced expression of CX3CR1 in a human monocyte line, and showed a reduction in the levels of specific mRNA between 72% and 96%.

Example 4

Analysis of the Gene Expression of p40 in a Human Monocyte Line

The capacity of the compounds to inhibit the expression of p40 by lipopolysaccharide (LPS)-stimulated MonoMac6 cells was evaluated. The cells were placed in 96-well plates at a concentration of 50 000 cells/well. The compounds were tested at the maximum soluble concentration given in Table 4 (in the range 30-300 µM) and incubated for 1 hour. The cells were then stimulated with LPS (100 ng/ml) for 4 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human p40 was used (Applied Biosystems, RefSeq NM_002187.2). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 4 below.

TABLE 4

| No. | % inhibition | [µM] |
|---|---|---|
| 1 | 32 | 150 |
| 10 | 65 | 30 |
| 17 | 37 | 150 |
| 18 | 39 | 75 |

As shown by the results obtained and given in Table 4, the compounds were capable of significantly inhibiting the LPS-induced expression of p40 in a human monocyte line, and showed a reduction in the levels of specific mRNA between 32% and 65%.

The invention claimed is:

1. A method of inhibiting expression of MCP-1, CX3CR1, or p40, the method comprising;
administering to a person in need thereof, an effective amount of a compound of formula (I):

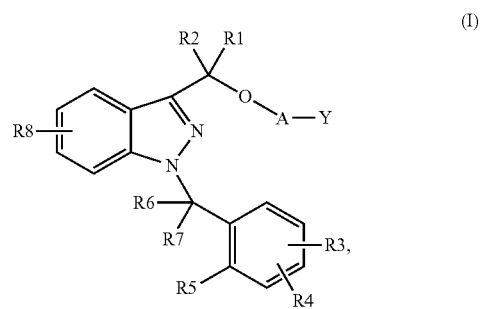

wherein
A is a σ bond, —$X_1$— or —$X_1$—O—$X_2$—, in which
$X_1$ and $X_2$, which may be identical or different from each other, are an alkyl group having from 1 to 5 carbon atoms, optionally substituted with one or more alkyl groups having from 1 to 5 carbon;
Y is H when A is a σ bond, or Y is H, —OH, or —N($R_{11}$)($R_{12}$) when A is $X_1$— or —$X_1$—O—$X_2$—, in which
$R_{11}$ is hydrogen, an alkyl group having from 1 to 5 carbon atoms, or $R_{11}$ together with
$R_{12}$ forms a 5- to 6-membered heterocycle,
$R_{12}$ is hydrogen, an alkyl group having from 1 to 5 carbon atoms, or $R_{12}$ together with
$R_{11}$ forms a 5- to 6-membered heterocycle;
$R_1$ and $R_2$, which may be identical or different from each other, are hydrogen or an alkyl group having from 1 to 5 carbon atoms;
$R_3$, $R_4$ and $R_8$, which may be identical or different from each other, are hydrogen, an alkyl group having from 1 to 5 carbon atoms, an alkoxy group having from 1 to 3 carbon atoms, a halogen atom, —OH, —N(R')(R''), —N(R')COR'', —CN, —CONR'R'', nitro, or trifluoromethyl;
with R' and R'', which may be identical or different from each other, being hydrogen or an alkyl group having from 1 to 5 carbon atoms;
$R_5$ is hydrogen, an alkyl group having from 1 to 5 carbon atoms, or $R_5$ together with one from between $R_6$ and $R_7$ forms a ring having 5 or 6 carbon atoms;
$R_6$ and $R_7$, which may be identical or different from each other, are hydrogen or an alkyl group having from 1 to 5 carbon atoms, or together form a group C=O, or one from between $R_6$ and $R_7$, together with $R_5$, forms a ring having 5 or 6 carbon atoms,
thereby inhibiting the expression of MCP-1, CX3CR1, or p40,
wherein a disease treatable by said inhibition is at least one disease selected from the group consisting of a metabolic syndrome, obesity, diabetes, insulin resistance, rheumatoid arthritis, arthritis induced by viral infections, psoriatic arthritis, arthrosis, lupus nephritis, diabetic nephropathy, glomerulonephritis, polycystic kidney disease, interstitial lung disease, fibrosis, multiple sclerosis, Alzheimer's disease, HIV-associated dementia, atopic dermatitis, psoriasis, vasculitis, restenosis, atherosclerosis, myocardial infarction, angina, acute coronary disease, a complication following surgical intervention, Crohn's disease, ulcerative colitis, a coronary disorder, and lupus erythematosus.

2. The method according to claim 1, wherein $X_1$ and $X_2$ are, independently of one another, an alkyl group having from 1 to 4 carbon atoms, optionally substituted with one or more alkyl groups having from 1 to 3 carbon atoms.

3. The method according to claim 1, wherein $X_1$ is selected from the group consisting of a $CH_2$ group, a $CH_2CH_2$ group, a $C(CH_3)_2$ group, and a $C(CH_3)_2CH_2$ group, and $X_2$ is selected from the group consisting of a $CH_2$ group, a $CH_2CH_2$ group, and a $CH_2CH_2CH_2$ group.

4. The method according to claim 1, wherein the residue A is selected from the group consisting of a σ bond, a $CH_2CH_2$ group, a $CH_2CH_2CH_2$ group, a $C(CH_3)_2CH_2$ group, a $CH_2CH_2OCH_2$ group, a $CH_2CH_2OCH_2CH_2$ group, and a $C(CH_3)_2CH_2OCH_2$ group, and a $C(CH_3)_2CH_2OCH_2CH_2$ group.

5. The method according to claim 1, wherein $R_{11}$ and $R_{12}$, which may be identical or different from each other, are a hydrogen atom, an alkyl group having from 1 to 3 carbon atoms, or together form a 6-membered heterocycle.

6. The method according to claim 1, wherein $R_1$ and $R_2$, which may be identical or different from each other, are a hydrogen atom, or an alkyl group having from 1 to 3 carbon atoms.

7. The method according to claim 1, wherein $R_3$ and $R_4$, which may be identical or different from each other, are selected from the group consisting of a hydrogen atom, an alkyl group having from 1 to 3 carbon atoms, an alkoxy group having 1 or 2 carbon atoms, an OH group, a nitro group, a trifluoromethyl group, a N(R')(R'') group, a —N(R')COR'' group, a —CN group, a —CONR'R'' group, $R_8$ is selected from the group consisting of a hydrogen atom, an alkyl group having from 1 to 3 carbon atoms, an alkoxy group having 1 or 2 carbon atoms, a Br atom, a Cl atom, an F atom, an OH group, a nitro group, a trifluoromethyl group, a N(R')(R'') group, a —N(R')COR'' group, a —CN group, a —CONR'R'' group, with R' and R'', which may be identical or different from each other, being a hydrogen atom or an alkyl group having from 1 to 3 carbon atoms.

8. The method according to claim 1, wherein $R_5$ is selected from the group consisting of a hydrogen atom, an alkyl group having from 1 to 3 carbon atoms, or $R_5$, together with one from between $R_6$ and $R_7$, forms a ring having 5 or 6 carbon atoms.

9. The method according to claim 1, wherein $R_6$ and $R_7$, which may be identical or different from each other, are a hydrogen atom, or an alkyl group having from 1 to 3 carbon atoms, or together form a group C=O, or one from between $R_6$ and $R_7$, together with $R_5$, forms a ring having 5 or 6 carbon atoms.

10. The method according to claim 1, wherein said disease is rheumatoid arthritis.

11. The method according to claim 1, wherein said disease is arthritis induced by viral infections.

12. The method according to claim 1, wherein said disease is lupus nephritis.

13. The method according to claim 1, wherein said disease is diabetic nephropathy.

14. The method according to claim 1, wherein said disease is glomerulonephritis.

15. The method according to claim 1, wherein said disease is polycystic kidney disease.

16. The method according to claim 1, wherein said disease is multiple sclerosis.

17. The method according to claim 1, wherein said disease is Alzheimer's disease.

18. The method according to claim 1, wherein said disease is HIV-associated dementia.

19. The method according to claim 1, wherein said disease is atopic dermatitis.

20. The method according to claim 1, wherein said disease is psoriasis.

21. The method according to claim 1, wherein said disease is restenosis.

22. The method according to claim 1, wherein said disease is, atherosclerosis.

23. The method according to claim 1, wherein said disease is acute coronary diseases.

24. The method according to claim 1, wherein said disease is Crohn's disease.

25. The method according to claim 1, wherein said disease is ulcerative colitis.

26. The method according to claim 1, wherein said disease is coronary disorders.

27. The method according to claim 1, wherein said disease is lupus erythematosus.

* * * * *